(12) United States Patent
Fielding et al.

(10) Patent No.: US 12,733,982 B2
(45) Date of Patent: Sep. 15, 2026

(54) IMAGE-GUIDED ROBOTIC SYSTEM FOR DETECTION AND TREATMENT

(71) Applicant: CENTRE FOR SURGICAL INVENTION AND INNOVATION, Hamilton (CA)

(72) Inventors: Timothy Scott Fielding, Hamilton (CA); Mehran Anvari, Hamilton (CA)

(73) Assignee: CENTRE FOR SURGICAL INVENTION AND INNOVATION, Hamilton (CA)

( * ) Notice: Subject to any disclaimer, the term of this patent is extended or adjusted under 35 U.S.C. 154(b) by 155 days.

(21) Appl. No.: 18/698,302

(22) PCT Filed: Oct. 4, 2022

(86) PCT No.: PCT/CA2022/051467
§ 371 (c)(1),
(2) Date: Apr. 3, 2024

(87) PCT Pub. No.: WO2023/056552
PCT Pub. Date: Apr. 13, 2023

(65) Prior Publication Data

US 2024/0423719 A1 Dec. 26, 2024

Related U.S. Application Data

(60) Provisional application No. 63/251,842, filed on Oct. 4, 2021.

(51) Int. Cl.

| | |
|---|---|
| ***A61B 34/10*** | (2016.01) |
| ***A61B 34/20*** | (2016.01) |
| ***A61B 34/30*** | (2016.01) |
| ***G06T 7/00*** | (2017.01) |

(52) U.S. Cl.
CPC .............. *A61B 34/10* (2016.02); *A61B 34/20* (2016.02); *A61B 34/30* (2016.02); *G06T 7/0012* (2013.01); *A61B 2034/2051* (2016.02); *G06T 2207/10088* (2013.01); *G06T 2207/20081* (2013.01);
(Continued)

(58) Field of Classification Search
CPC ......... A61B 34/10; A61B 34/20; A61B 34/30; A61B 2034/2051; A61B 5/4381; A61B 5/4887; A61B 5/7267; A61B 10/0241; A61B 2018/00333; A61B 2018/00547; A61B 2576/02; A61B 10/0233; A61B 2034/107; A61B 2090/374; A61B 2090/3954; A61B 5/055; A61B 18/02; G06T 7/0012; G06T 2207/10088; G06T 2207/20081; G06T 2207/30081; G06T 2207/30096; G06N 3/0464; G06N 3/09; G01R 33/5601; G01R 33/5608;
(Continued)

(56) References Cited

U.S. PATENT DOCUMENTS

| | | | | |
|---|---|---|---|---|
| 2019/0156477 | A1* | 5/2019 | Perrin | A61B 5/055 |
| 2020/0250817 | A1* | 8/2020 | Leng | G06T 7/0012 |
| 2022/0265343 | A1* | 8/2022 | Onik | A61B 18/1477 |

* cited by examiner

*Primary Examiner* — Joel Lamprecht
(74) *Attorney, Agent, or Firm* — Norton Rose Fulbright Canada LLP

(57) ABSTRACT

There is provided a system and method for screening, classifying and diagnosing lesions. Machine learning models and AI models may be trained to automatically classify and diagnose lesions. A surgical robot may be configured to perform biopsies and treatments on lesions.

14 Claims, 6 Drawing Sheets

(52) U.S. Cl.
CPC ............... *G06T 2207/30081* (2013.01); *G06T 2207/30096* (2013.01)

(58) Field of Classification Search
CPC .......... G01R 33/5602; G01R 33/56341; G16H 20/40; G16H 30/40; G16H 50/20
See application file for complete search history.

Figures 5A, 5B, 5C:
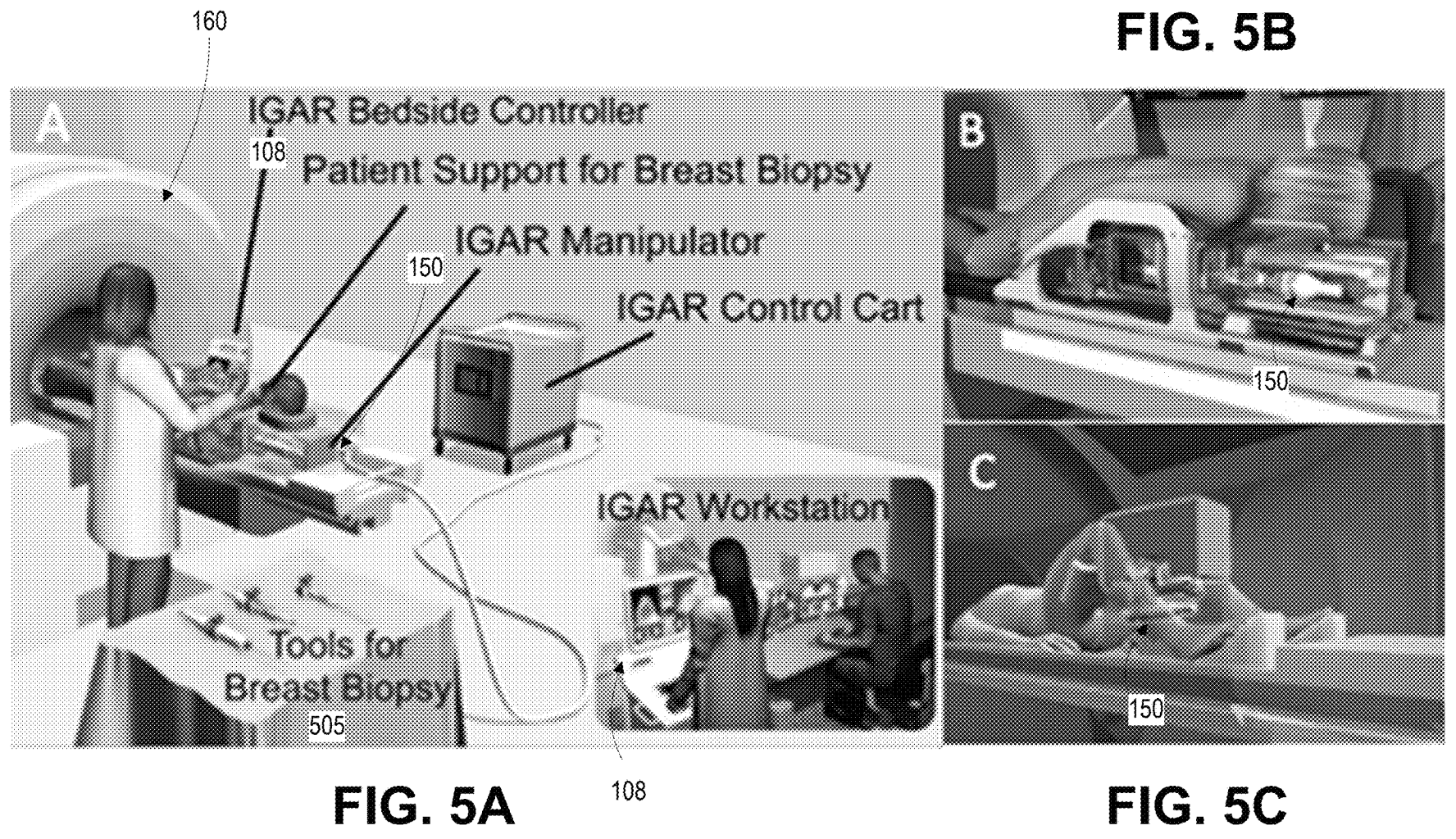

IGAR Bedside Controller

Patient Support for Breast Biopsy

IGAR Manipulator

150

IGAR Control Cart

IGAR Workstation

108

Tools for Breast Biopsy

505

IMAGE-GUIDED ROBOTIC SYSTEM FOR DETECTION AND TREATMENT

CROSS-REFERENCE TO RELATED APPLICATIONS

This application claims the benefit of U.S. Provisional Patent Application No. 63/251,842, filed on Oct. 4, 2021, the entire contents of which are incorporated by reference herein.

FIELD

This relates generally to robotic systems for detecting and treating cancers, and in particular to robotic systems which use artificial intelligence.

BACKGROUND

For both medical professionals and patients, the processes associated with cancer screening, diagnosis and treatment may be long, complex, and difficult to navigate. These challenges add unnecessary stress to patients, and may be worsened by a lack of access and/or undue delays in accessing the highly specialized care required from, for example, imaging specialists, oncologists, interventionalists, and surgeons. This may be exacerbated for patients in rural and remote regions, which may lack the equipment and expertise required altogether, necessitating travel in order to access proper healthcare.

Accordingly, there is a need for systems which may reduce the time required for obtaining proper care and/or treatment for various types of cancers. It would also be beneficial to be able to provide more accessible care to patients in remote areas, which often lack the specialized care available in urban centres.

SUMMARY

According to an aspect, there is provided a method of diagnosing and treating a patient, the method comprising: training, using a first training data set, a machine learning classifier to detect lesions in MR images of an organ; training, using a second training data set, an artificial intelligence (AI) model to determine malignancy of a lesion; obtaining one or more magnetic resonance (MR) images of an organ of a patient; identifying a lesion in the organ of the patient and a probability of malignancy by applying the machine learning classifier to the obtained one or more MR images of the organ of the patient; determining, based on the probability of malignancy, whether to perform a biopsy on the identified lesion of the organ of the patient; determining a diagnosis for the identified lesion by applying the AI model to the obtained one or more MR images of the organ of the patient; determining, based on the diagnosis, a surgical treatment pathway for the lesion; and performing, by a surgical robotic device, a treatment on the lesion based on the determined surgical treatment pathway.

According to another aspect, there is provided a system for diagnosing and treating a patient, the system comprising: one or more processors; one or more computer-readable storage media having stored thereon processor-executable instructions that, when executed by said one or more processors, cause the one or more processors to perform a method comprising: training, using a first training data set, a machine learning classifier to detect lesions in MR images of an organ; training, using a second training data set, an artificial intelligence (AI) model to determine malignancy of a lesion; obtaining one or more magnetic resonance (MR) images of an organ of a patient; identifying a lesion in the organ of the patient and a probability of malignancy by applying the machine learning classifier to the obtained one or more MR images of the organ of the patient; determining, based on the probability of malignancy, whether to perform a biopsy on the identified lesion of the organ of the patient; determining a diagnosis for the identified lesion by applying the AI model to the obtained one or more MR images of the organ of the patient; determining, based on the diagnosis, a surgical treatment pathway for the lesion; and performing, by a surgical robotic device, a treatment on the lesion based on the determined surgical treatment pathway.

Other features will become apparent from the drawings in conjunction with the following description.

BRIEF DESCRIPTION OF DRAWINGS

In the figures which illustrate example embodiments,

FIG. 5A is a rendering of an example medical robot system as depicted in FIG. 1;

FIG. 5B is a rendering of an example medical robotic system configured to perform breast screenings, biopsies, and treatments;

FIG. 5C is a rendering of an example medical robotic system configured to perform prostate screenings, biopsies and treatments.

DETAILED DESCRIPTION

Certain types of cancers may be more prevalent than others, and may be more straightforwardly treated than other types of cancer. For example, in Canada, prostate cancer accounts for roughly 20% of new cancers in biological males, and breast cancer accounts for 25% of new cancers in biological females. Notably, among the transgender population (an already stigmatized group which faces additional barriers to healthcare), hormone treatments may increase the risk of both breast and prostate cancer.

Wait times for a referral to medical or radiation oncology may be lengthy (for example, 4-5 weeks in Canada), and the wait times for surgical treatment may be even longer. Such delays and decreased access to physicians can be detrimental to cancer care. For example, a typical course of treatment for breast cancer or prostate cancer may require at least 5 visits to healthcare professionals from screening to treatment. Associated delays increase the stress experienced by patients, and delays may lower the survival rates of more advanced cancers.

Early detection and treatment of breast and prostate cancers may allow for less invasive treatments, such as cryoablation and brachytherapy. Contrastingly, treatment of more advanced breast and prostate cancers may require invasive and complex surgical interventions such as mastectomies and prostatectomies, which further emphasizes the importance of early diagnosis and treatment.

Some embodiments described herein relate to an autonomous robotic system configured to streamline and expedite the cancer care pathway by allowing for one-step screening, diagnosis and treatment of early breast and prostate cancers. Some embodiments may render screening, diagnosis and treatment of early cancers more accessible. Some embodiments use artificial intelligence (AI) to perform diagnosis and treatment by combining AI image analysis and histopathology capabilities with robotic intervention technology. Some embodiments may perform biopsies and/or treatments using an Image-Guided Automated Robot (IGAR), such as that described in, for example, U.S. Pat. No. 9,259,271, the entire contents of which are incorporated herein by reference.

Figure 1:
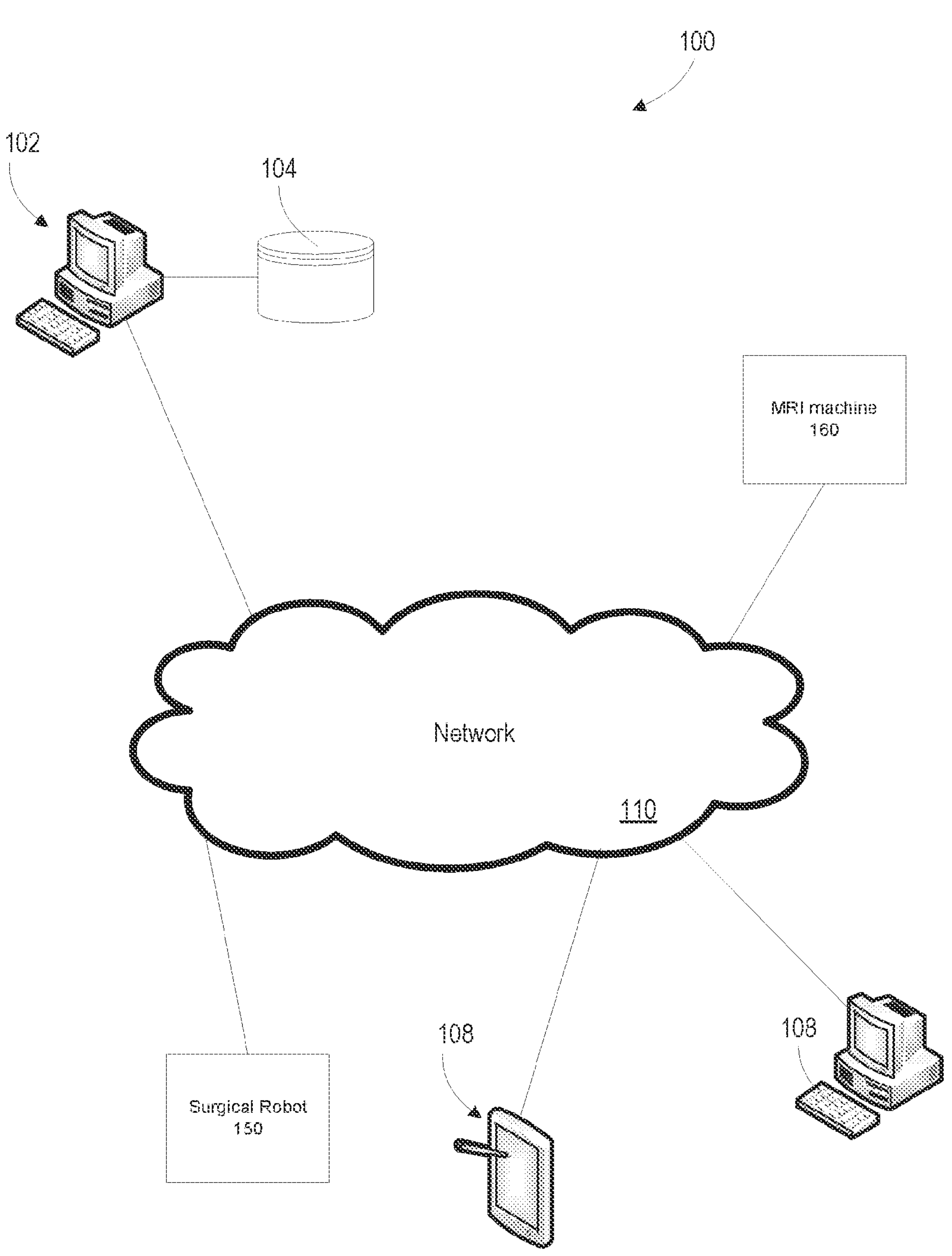
FIG. 1 is a block diagram depicting components of an example medical robotic system.

Various embodiments of the present invention may make use of interconnected computer networks and components. FIG. 1 is a block diagram depicting components of an example robotic system 100. As used herein, the term "robotic system" refers to a combination of hardware devices configured under control of software and interconnections between such devices and software. Such systems may be operated by one or more users or operated autonomously or semi-autonomously once initialized.

As depicted, system 100 includes at least one server 102 with a data storage 104 such as a hard drive, array of hard drives, network-accessible storage, or the like; a plurality of client computing devices 108, and a magnetic resonance imaging (MRI) machine 160, and a surgical robot 150. Server 102, client computing devices 108, MRI machine 160 and surgical robot 150 are in communication by way of a network 110. More or fewer of each device are possible relative to the example configuration depicted in FIG. 1. In some embodiments, surgical robot 150 may be implemented as an IGAR, such as that described in, for example, U.S. Pat. No. 9,259,271.

FIG. 5A is a rendering of an example robotic system 100. As depicted, a patient is laying in the vicinity of MRI machine 160, and surgical robot 150 is positioned to perform one or more actions on the patient. Client computing devices are being used by various parties to view recorded images and to control surgical robot 150 and MRI machine 160. In some embodiments, a client device 108 may communicate with IGAR control cart (another computing device), which may translate commands into control instructions for moving surgical robot 150.

In some embodiments, surgical robot 150 is an image-guided robot configured to perform needlescopic interventions with high precision. Surgical robot 150 may be designed to function within an MRI environment, and configured to perform MRI-guided breast biopsies and prostate biopsies. Surgical robot 150 may have built-in magnetic resonance fiducial markers, which allow surgical robot 150 to register MR images of the patient within a manipulator of surgical robot 150.

In some embodiments, surgical robot 150 may include a breast patient support (as shown in FIGS. 5A and 5B) which facilitates positioning the patient and providing space for a manipulator of surgical robot 150 to be repositioned during treatment. A breast compression system may position any immobilize the patient's breast within a support structure above the MR fiducial markers, and built-in RF coils may enable MR imaging.

Network 110 may include one or more local-area networks or wide-area networks, such as IPv4, IPV6, X.25, IPX compliant, or similar networks, including one or more wired or wireless access points. The networks may include one or more local-area networks (LANs) or wide-area networks (WANs), such as the internet. In some embodiments, the networks are connected with other communications networks, such as GSM/GPRS/3G/4G/LTE networks.

As shown, server 102 may provide web server functionality. In some embodiments, a web server may be implemented on a separate computing device from server 102.

As will be described in further detail, server 102 may be connected to a data storage 104. In some embodiments, a web server may host a website accessible by client computing devices 108. Web server is further operable to exchange data with server 102 such that data associated with client computing devices 108, surgical robot 130, and/or MRI machine 160 can be retrieved from server 102 and utilized in accordance with the systems and methods herein. For example, client computing devices 108 may be used to send control instructions to surgical robot 150 and/or MRI machine 160.

Server 102 may be based on Microsoft Windows, Linux, or other suitable operating systems. Client computing devices 108 may be, for example, personal computers, smartphones, tablet computers, or the like, and may be based on any suitable operating system, such as Microsoft Windows, Apple OS X or iOS, Linux, Android, or the like.

In some embodiments, a technician on-site with the MRI machine 160 and/or surgical robot 150 may use a client device 108 to communicate with an off-site expert (e.g. a radiologist or other specialist) using another client device 108 via network 110.

Figure 2:
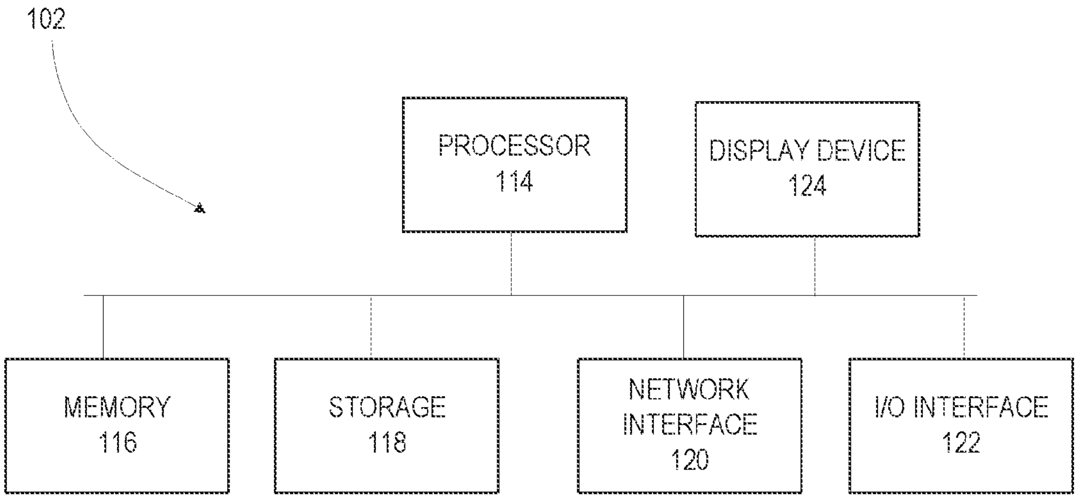
FIG. 2 is a block diagram depicting components of an example server or client computing device.

FIG. 2 is a block diagram depicting components of an example server 102 or client computing device 108. As depicted, each server 102 and client device 108 includes a processor 114, memory 116, persistent storage 118, network interface 120, and input/output interface 122.

Processor 114 may be an Intel or AMD x86 or x64, PowerPC, ARM processor, or the like. Processor 114 may operate under the control of software loaded in memory 116. Network interface 120 connects server 102 and client computing device 108 to network 110. Network interface 120 may support domain-specific networking protocols for surgical robot 150 and/or MRI machine 160. I/O interface 122 connects server 102 or client computing device 108 to one or more storage devices (e.g. storage 104) and peripherals such as keyboards, mice, pointing devices, USB devices, disc drives, display devices, and the like. In some embodiments, I/O interface 122 may directly connect server 102 and/or computing device 108 to surgical robot 150 and/or MRI machine 160.

In some embodiments, I/O interface 122 connects various sensors and other specialized hardware and software used in connection with the operation of surgical robot 150 and/or MRI machine 160 to processor 114 and/or to other computing devices 102, 108. In some embodiments, I/O interface 122 may be used to connect surgical robot 150 and/or MRI machine 160 to other computing devices 102, 106, 108 and provide access to various sensors and other specialized hardware and software within surgical robot 150 and/or MRI machine 160.

Software may be loaded onto server 102 or client computing device 108 from peripheral devices or from network 110. Such software may be executed using processor 114.

Figure 3:
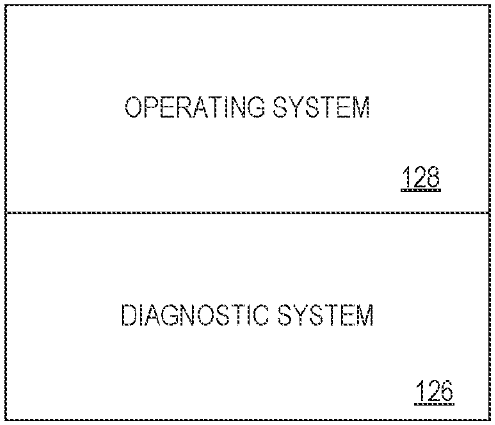
FIG. 3 depicts a simplified arrangement of software at a server or client computing device.

FIG. 3 depicts a simplified arrangement of software at a server 102 or client computing device 108. The software may include an operating system 128 and application software, such as diagnostic system 126. Diagnostic system 126 is configured to interface with, for example, one or more systems or subsystems of server 104, surgical robot 150, and/or MRI machine 160, and to send control signals (e.g. control parameters for movements) to surgical robot 150. In some embodiments, diagnostic system 126 is further configured to accept data and signals from server 102 or data storage 104 (e.g. historical imaging data and known diagnoses for generating machine learning models), MRI machine 160 (e.g. imaging results), and surgical robot 150 (e.g. positioning parameters).

Figure 4A:
FIG. 4A is a flow diagram depicting a traditional workflow for screening and treating breast and/or prostate cancers.
Figure 4A:
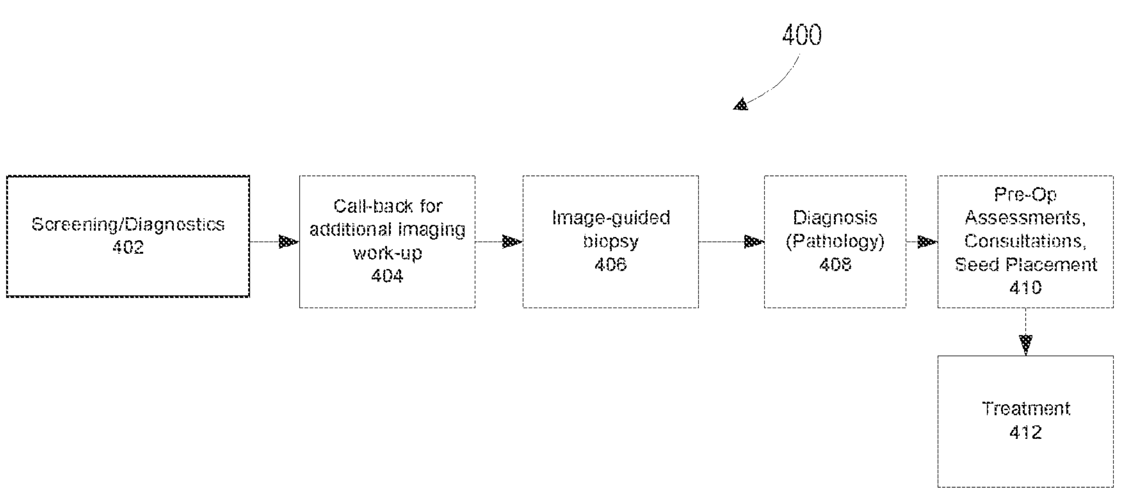

FIG. 4A is a flow diagram depicting the current workflow 400 for screening and treating breast and/or prostate cancers. Although this disclosure predominantly makes reference to treating breast cancer and/or prostate cancer, it is contemplated that systems and methods described herein may be applied to other types of cancers (e.g. kidney cancer, other and/or all solid tumors, and the like).

Workflow 400 begins with screening/diagnosis 402 by a healthcare professional for breast cancer or prostate cancer. At 404, the patient may be called back for additional imaging work-ups. At 406, an image-guided biopsy may be performed to remove a sample of a lesion. At 408, the biopsy sample is diagnosed. At 410, pre-operation assessments, consultations, and seed placement may be performed. Finally, at 412, the patient receives treatment (e.g. cryoablation or brachytherapy in the case of early breast and prostate cancers, respectively).

As depicted, process 400 in FIG. 4A may require between 5-7 different appointments, and typically spans a time period of roughly 4 to 10 weeks.

Figure 4B:
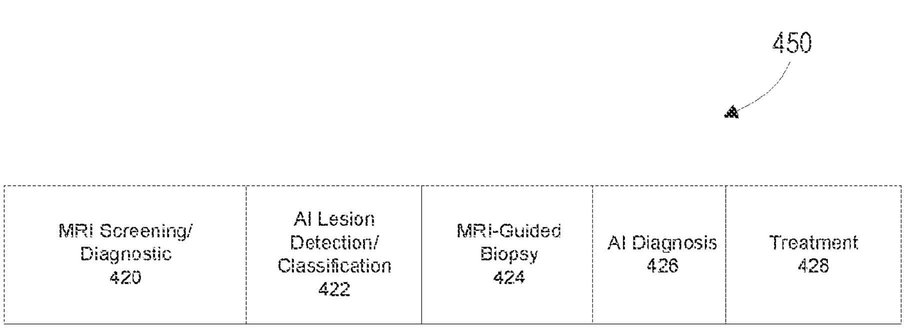
FIG. 4B is a flow diagram depicting an abbreviated workflow for screening and treating breast and/or prostate cancers according to some embodiments of the invention.

FIG. 4B is a flow diagram depicting an improved, abbreviated workflow 450 for screening and treating breast and/or prostate cancers according to some embodiments of the invention. In some embodiments, all of workflow 450 may be performed in one appointment, rather than the longer and more drawn-out workflow 100. In some embodiments, abbreviated workflow may be appropriate for patients without a history of prior cancer and having early, single site lesions that are localized to the organ (e.g. breast or prostate) and less than or equal to 1 cm in the case of breast lesions, and less than or equal to 60 mm in the case of prostate lesions.

At 420, an MRI screening process is performed by MRI machine 160. In the case of breast scans, the patient may be screened with an abbreviated MRI protocol which may reduce time and cost. In some embodiments, the abbreviated MRI protocol may include T2-weighted and T1-weighted pre-contrast imaging, and may be followed by a single post-contrast sequence.

In the case of prostate scans, block 420 may include MRI machine 160 performing multiparametric MRI (mpMRI) for patients elevated serum prostate-specific antigen (PSA). mpRMI may include the use of T2 and diffusion-weighted images and/or dynamic contrast enhanced (DCE) imaging to improve diagnostic accuracy.

At 422, one or more machine learning algorithms are applied to the MRI images obtained at block 420. In some embodiments, an ML model may be used to detect suspicious lesions based on the images obtained at block 420 and at least one machine learning model. In some embodiments, the ML model may determine a probability or degree of suspicion that a lesion is cancerous.

In some embodiments, if the degree of suspicion or probability are above a threshold (e.g. 90%), system 126 may generate an instruction set for surgical robot 150 to perform an MRI-guided robotic biopsy 424 on the suspicious lesion. In some embodiments, In some embodiments, if the degree of suspicion is below a threshold (e.g. 90%), system 126 might not perform an MRI-guided robotic biopsy and instead perform a diagnosis using AI-histopathology 426. In some embodiments, system 126 may perform both MRI-guided robotic biopsy 424 and AI diagnosis 426 in It should be appreciated that the threshold suspicion for deciding whether to perform an MRI-guided robotic biopsy 424 may be need not be 90% and can be any suitable threshold value. Moreover, the threshold suspicion may be confirmed and adjusted based on clinical experience and/or resulting biopsy results (which may in turn be used to refine the ML models which are used to determine the suspicion value).

In some embodiments, MRI-guided robotic biopsy 424 may be performed by having the patient placed outside the magnetic resonance bore and on the table. When the patient is so positioned, system 100 is configured to calculate a pathway to the suspicious lesion identified at 422. In some embodiments, a technician present may be instructed to attach an anaesthesia needle/tool adaptor to surgical robot 150 to deliver accurate and precise freezing and/or numbing to areas of the patient forming part of the pathway. Once the patient has been anesthetized, an introducer cannula may be inserted through the patient's skin. In some embodiments, the tip of the cannula may be located at or in the immediate vicinity of the suspicious lesion.

Once the arm of the surgical robot 150 has been placed with the tip of the cannula in proximity to the suspected lesion (as depicted in FIGS. 5A and 5B), an MR-safe sheath may remain in place to act as a pathway for tools required for the subsequent procedure. In some embodiments, MRI machine 160 may be used to confirm the correct placement of the cannula.

Once the correct placement of the cannula has been confirmed, a biopsy 505 tool may be attached to surgical robot 150 and a biopsy of the suspected lesion may be performed. Optionally, depending on the size of the suspected lesion, MRI machine 160 may capture further images to conform that the biopsy was performed successfully.

FIG. 5C is a rendering of a configuration of system 100 for performing prostate screenings and biopsies. As depicted, a manipulator of surgical robot 150 may be docked to a prostate-specific patient support that may tilt the patient's pelvis to support perineal access of a needle insertion. Although manual ultrasound-guided biopsies are often performed transrectally, some embodiments described herein allow for the perineal approach, which may be safer and preferred, and may allow for simultaneous targeted therapy.

Patients may be stabilized in the MRI device 160 while performing either of a prostate biopsy and/or brachytherapy. MR image-able fiducial markers may form part of the patient support, and may be connected to the surgical robot 150 to facilitate capturing MR images.

In some embodiments, AI diagnosis 426 is performed using one or more of a) Gleason Score group grading via virtual biopsy (for prostate) and b) ex-vivo digitized histopathology (for breast and/or prostate).

In some embodiments Gleason score group grading may be performed by using MR images together with ML models to arrive at a diagnosis, as explained further below.

In some embodiments, ex-vivo digitized histopathology comprises performing AI analysis of digitized ex-vivo histopathology. In some embodiments, confocal microscopy images of tissue may be processed to yield substantially equivalent tissue staining relative to standard haematoxylin and eosin (HE). These digitized specimens may then be analyzed for tissue classification using computer vision techniques (for example, segmentation tasks) and diagnosed using, for example, deep learning techniques.

After the suspicious lesion has been diagnosed at block 426, system may then perform treatment 428. In some embodiment, treatment makes use of Artificial Intelligence and/or Machine Learning. In some embodiments, treatment 428 may be performed if a lesion is determined to be cancerous and/or pre-cancerous. In some embodiments, system 126 may generate a treatment plan for execution. In some embodiments, a treatment plan may include a series of instructions for a user to attach various treatment tools to surgical robot 150, as well as control instructions for navigating surgical robot 150 through a pathway to be in a proper position to perform the treatment 428. In some embodiments, patient MRI images obtained at 420 may be used as guidance inputs to the surgical robot 150's positioning system. In some embodiments, an AI-based interface is used with patient MRI images to provide guidance inputs to surgical robot 150.

In some embodiments, treatment 428 may include performing cryoablation (for breast cancer). In some embodiments, treatment 428 may include brachytherapy (for prostate cancer). In some embodiments, an additional MRI-guided biopsy 424 may be performed by surgical robot 150 after treatment 428 to confirm the adequacy of treatment 428. For example, the additional MRI-guided biopsy 424 may determine whether adequate margins were achieved with the iceball following cryoablation, and/or whether seed placement was accurate following brachytherapy.

Figure 6:
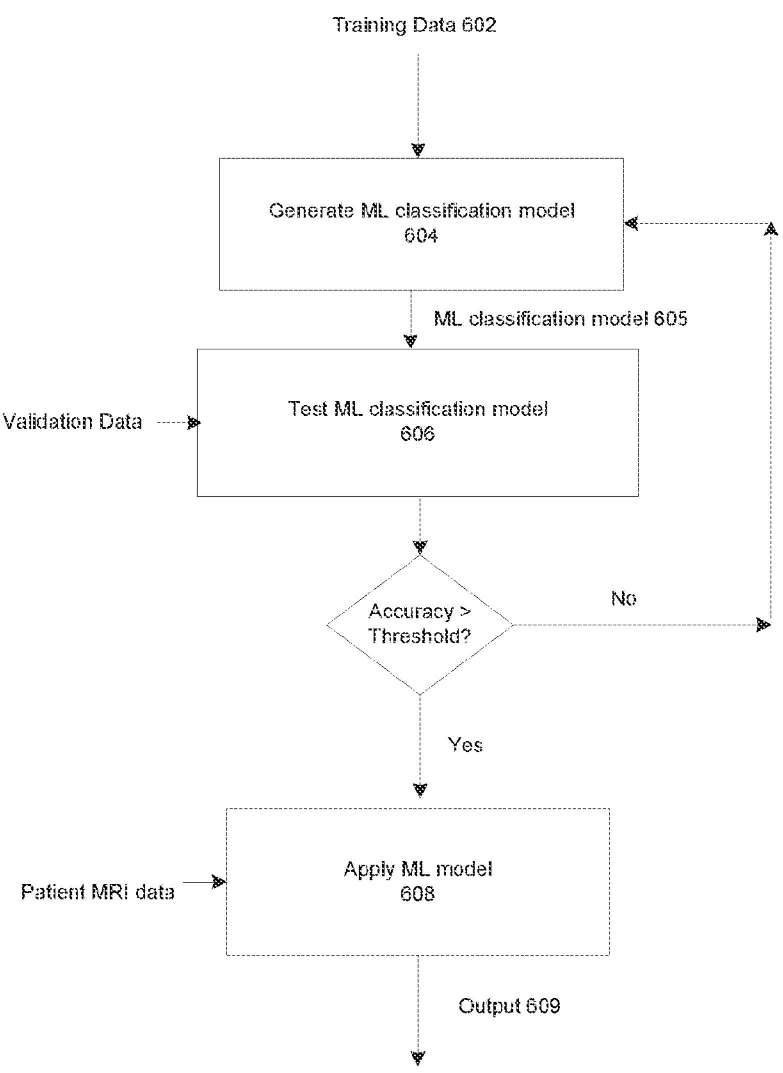
FIG. 6 is an illustration of an example process for ML detection of lesions.

Some embodiments make use of AI and machine learning (ML) at block 422 to detect lesions in a patient's MRI images. FIG. 6 is an illustration of an example process for ML detection of lesions. The development of an ML classification system typically requires training data to train an ML model. In some embodiments, some or all data used to train ML models may be anonymized.

To increase the likelihood of higher quality segmentation of abnormal findings and resulting classifications, a large training data 602 set is preferable. For example, a training data set of 10,000 breast MR studies with known pathology and outcomes may be used. In some embodiments, outcomes may include one or more of BI-RADS (Breast Imaging-Reporting and Data System) scores, normal assessment with a 1-2 year follow up, and/or malignant/benign biopsies with Gleason scores). For breast lesion detection, training data 602 may comprise T2 weighted imaging (with and/or without fat suppression), as well as a DCE T1 weighted imaging sequence including a pre-contrast image and multiple post-contrast images.

In the case of prostate cancer detection, an example training data 602 set may include 5000 prostate MR studies with known pathology and outcomes. In some embodiments, outcomes may include PI-RADS (Prostate Imaging-Reporting and Data System) scores, normal assessment with 1-2 years follow up, and/or malignant/benign biopsies with Gleason scores. In some embodiments, each prostate MR study may include one or more of T2 weighted, diffusion weighted, and/or DCE images.

In some embodiments, to improve the likelihood of diversity and relevance, anonymized data sets may be collected from international sources (e.g. local hospital sources as well as international sources). In some embodiments, breast cancer training data may include data covering the full range of malignant lesions, and benign lesions including high risk benign legions, and as many cases or rare and challenging conditions as possible.

In some embodiments, it may be necessary to pre-process prostate and/or breast MR studies to ensure training data 602 has a consistent format. Consistent formatting within training data 602 may be important for ensuring accuracy of resulting ML models.

At 604, an ML classification model is trained based on training data 602. For example, an ML classification model can be trained for identifying suspicious lesions in a patient's breast MR images. A separate ML classification model can be trained for identifying suspicious lesions in a patient's prostate MR images.

In some embodiments, prostate ML classification models may be validated 606 using a previously imaged and validated data set. For example, for prostate lesion ML detection, an example validation data set may include previously imaged and validated ML techniques for lesion characterization in prostate cancer on mpMRI and prostate specific membrane antigen (PSMA) positron emission tomography (PET) imaging. Such an example validation data set may include pre-surgical mpMRI and PSMA PET images obtained prior to prostatectomy, as well as accurate co-registered to pathologist-annotated whole-mount digital histology images of excised tissue on which cancer has been completely mapped and graded. In some embodiments, ML model 605 may be refined and/or adjusted if the accuracy of ML 605 when applied to validation data does not meet a threshold accuracy.

In some embodiments, an ML classification model 605 may receive a breast or prostate MR study as an input and produce an output 609. In some embodiments, output 609 is an anatomical segmentation of the imaging volume and a list of any abnormal findings detected. In some embodiments, each abnormal finding may contain location information and an associated probability of malignancy and BI-RADS or PI-RADS scores (depending on the type of cancer). Output 609 may then be used in determining whether to perform a biopsy at 424 or whether to proceed without a biopsy to AI diagnosis 426. For example, the decision of whether to perform a biopsy may be based on the probability of malignancy and/or BI-RADS/PI-RADS scores output by the ML model 605.

In some embodiments, automated deep learning algorithms may identify nodal metastases in histopathological analysis of breast tissue better than an expert pathologist panel, and assess mammograms equally as well as expert radiologists, with a 5.7% and 9.4% reduction in false positive and false negative rates, respectively.

In some embodiments, ML model 605 may be implemented as a pipeline of deep learning models for anatomical segmentation and detection of abnormal findings may be implemented for breast MR analysis. An example pipeline of deep learning modules may include one or more of:

| Module | Description | Output |
|---|---|---|
| DICOM (Digital Imaging and Communications in Medicine) Study Manager | Acquired series and views are identified, organized, appropriate ones selected and sent to subsequent modules for processing. | Selected series |
| Quality Assurance | Set of AI classification algorithms run to determine if the exam is of sufficient technical quality to be evaluated, and if the patient should be excluded | If false, stop |
| Series Registration | Volumes in DCE series registered for motion correction and inter-series registration done for label propagation across series. | Registered series |
| Anatomic Segmentation | Each pixel in the imaging volume classified using a semantic segmentation model. Classes for breast: air, thoracic cavity, abdomen, chest wall, breast tissue, axilla, and possibly classes as required for robotic biopsy planning (e.g. nipple, blood vessels). Classes for prostate: gland localized and segmented, followed by lesion segmentation on detection. General algorithm development strategy: implement and evaluate best published approach to define a dataset baseline performance, iteratively refine model to achieve required performance level. | Anatomical map for robotic biopsy planning |
| Abnormal Finding: Detection and Segmentation | Sub-volume containing breast or prostate tissue evaluated for abnormal findings. Abnormal regions of tissue segmented. Establish benchmark performance on dataset using U-Net style semantic segmentation networks, explore more modern semantic segmentation architectures with demonstrated improved performance on large-scale computer vision datasets. | List of abnormal findings with location |
| Abnormal Finding: Classification | Dedicated patch classifier trained for a “second look” at regions identified as abnormal, classify abnormal finding based on PoM in terms of a BI-RADS/PI-RADS classification. | PoM and BI-RADS/PI-RADS classification |

In some embodiments, upon identifying a suspicious target in a patient's MR study, the suspicious target's coordinates and structures required to plan MRI-guided biopsy 424 may be routed to system 126 to generate a surgical plan or pathway for surgical robot 150 to execute a biopsy or therapy. In some embodiments, once surgical robot is moved into position to perform the biopsy or therapy, a confirmation image may be taken to confirm that surgical robot 150 is in the correct position. Once the biopsy 424 and/or treatment 428 is complete, a confirmatory image may also be taken.

As described above, some embodiments perform AI diagnosis 426 using AI histopathology. In some embodiments, AI diagnosis 426 may include Gleason scores using virtual pathology for prostate cancer. In other embodiments, AI diagnosis may include ex-vivo digitized histopathology using confocal microscopy and machine learning for prostate and breast cancer.

In some embodiments, ex-vivo digitized histopathology includes protocols for obtaining H&E stain equivalent slides images from biopsied tissue samples using confocal microscopy. In some embodiments, a digital pathology platform may then be used to identify tumor cells in samples using computational pathology. The system may evaluate biological characteristics including, but not limited to, receptor status (ER/PR/HER2), tumor grade, proliferative index, and presence of invasive vs. *in situ* disease in tissue specimens.

In some embodiments, Gleason scoring may use a database of MR studies as training data which includes pathology information for prostate legions. Convolutional Neural Networks (CNNs) may be trained to learn lesion characteristics through leveraging imaging across multi-modal images (e.g. T2, DWI, DCE) for predicting legion malignancies. The resulting CNNs may find correlations between PI-RADS and Gleason scores, as well as exploit complementary information in each modality (e.g. T2, DWI, DCE). For example, T2 images may provide information about lesion location and overall appearance (e.g. intensity, homogeneity, shape, or the like), DWI and apparent diffusion coefficient (ADS) may provide information about Brownian motion of water molecules within lesions, and DEC images may represent lesion response to contrast agents in different phases (e.g. early, peak, late).

In some embodiments, for ex-vivo digital histopathology, concurrent recruitment and analyses may be performed on breast and prostate specimens to identify invasive carcinomas. Other histological information may include Nottingham grading and receptor status assessments from core biopsies obtained from breast cancer and prostate cancer patients during surgeries. In some embodiments, samples may be evaluated by experts for ground truth labelling. After confocal imaging, specimens may be submitted for formalin-fixed paraffin embedding and sectioning with a pathologist's clinical assessments of the HE-stained slides used as the reference standard for training and testing the CNNs.

The resulting AI models (e.g. CNNs) may be tested against validation data and on future biopsy results to correlate results between AI histopathology and biopsy-derived histopathology, which allows for continuing training and improvement of resulting models.

Although the present disclosure describes example embodiments which make use of treatments such as biopsies, cryoablation and brachytherapy, these are merely example treatments. For example, it is contemplated that the systems and methods described herein may apply to other imaging modalities, including but not limited to ultrasound and tomosynthesis, as well as other ablative options useful for treating other cancers.

It will be appreciated that use of surgical robot 150 and system 100 more broadly may allow medical interventions to be performed without a highly trained specialist on site, and can instead be supervised remotely via video control, thereby providing access to minimally invasive needlescopic interventions that are proven options to treat early breast and prostate cancers to patients outside of urban centers.

It will be further appreciated that some embodiments described herein may greatly reduce the amount of time required to screen, diagnose and treat certain cancers, particularly at early stages. This allows for more invasive and expensive surgical procedures to be avoided, and for minimally invasive, effective treatments to be carried out quickly upon identifying a lesion of concern.

Although the present disclosure makes reference to breast cancer and prostate cancer in particular, these are merely examples. It is contemplated that systems and methods described herein may be applicable to treatment of other forms of cancer (for example, liver, kidney, and lung, to name but a few other examples).

Of course, the above-described embodiments are intended to be illustrative only and in no way limiting. The described embodiments are susceptible to many modifications of form, arrangement of parts, details, and order of operation. The invention is intended to encompass all such modifications within its scope, as defined by the claims.

What is claimed is:

1. A method of diagnosing and treating a patient, the method comprising:

training, using a first training data set, a machine learning classifier model to detect lesions in magnetic resonance (MR) images of an organ, wherein said machine learning classifier model is implemented as a pipeline of deep learning modules, said deep learning modules including an anatomical segmentation module configured to generate an anatomical map, an abnormal finding detection and segmentation module, and an abnormal finding classification module;

obtaining one or more magnetic resonance (MR) images of an organ of a patient;

applying the machine learning classifier model to the obtained one or more MR images of the organ of the patient to obtain an output comprising an anatomical segmentation of an imaging volume and location information and an associated probability of malignancy for a lesion;

determining, based on the probability of malignancy, whether to perform an MRI-guided biopsy on the lesion of the organ of the patient;

determining a diagnosis for the identified lesion by applying an AI diagnosis model to the obtained one or more MR images of the organ of the patient;

determining, based on the diagnosis, a treatment plan for said lesion, said treatment plan including a series of instructions for a user to attach one or more treatment tools to a surgical robotic device and control instructions for navigating said surgical robotic device through an in-bore pathway to be positioned to perform an in-bore treatment on the lesion; and performing, by said surgical robotic device, said in-bore treatment on the lesion based on the treatment plan.

2. The method of claim 1, wherein the organ is one of a breast or a prostate.

3. The method of claim 1, wherein the AI diagnosis model is based on ex-vivo digitized histopathology.

4. The method of claim 2, wherein the AI diagnosis model is based on Gleason scoring using a machine learning model and the MR images of the prostate.

5. The method of claim 1, wherein the MRI-guided biopsy on the identified lesion is performed by the surgical robotic device when the probability of malignancy exceeds a threshold probability.

6. The method of claim 5, wherein the diagnosis for the identified lesion is determined by applying the AI diagnosis model to the obtained one or more MR images and a sample from the biopsy.

7. The method of claim 1, wherein the treatment is cryoablation.

8. The method of claim 1, wherein the treatment is brachytherapy.

9. The method of claim 5, wherein performing the MRI-guided biopsy with the surgical robotic device comprises generating a set of control instructions and transmitting the set of control instructions to the surgical robotic device.

10. The method of claim 1, wherein the first training data includes a plurality of MR studies with known pathologies and outcomes.

11. The method of claim 10, wherein said outcomes include one or more of BI-RADS scores, PI-RADS scores, and/or malignant/benign biopsies with Gleason scores.

12. The method of claim 1, wherein the output from the machine learning classifier model is an anatomical segmentation of the one or more MR images, a listing of one or more abnormal findings detected in the one or more MR images.

13. The method of claim 12, wherein each of the one or more abnormal findings includes location data and the probability of malignancy and/or a BI-RADS or PI-RADS score.

14. A system for diagnosing and treating a patient, the system comprising:

one or more processors;

a surgical robotic device;

one or more computer-readable storage media having stored thereon processor-executable instructions that, when executed by said one or more processors, cause the one or more processors to perform a method comprising:

training, using a first training data set, a machine learning classifier model to detect lesions in magnetic resonance (MR) images of an organ, wherein said machine learning classifier model is implemented as a pipeline of deep learning modules, said deep learning modules including an anatomical segmentation module configured to generate an anatomical map, an abnormal finding detection and segmentation module, and an abnormal finding classification module;

obtaining one or more MR images of an organ of a patient;

applying the machine learning classifier model to the obtained one or more MR images of the organ of the patient to obtain an output comprising an anatomical segmentation of an imaging volume and location information and an associated probability of malignancy for a lesion;

determining, based on the probability of malignancy, whether to perform an MRI-guided biopsy on the lesion of the organ of the patient;

determining a diagnosis for the identified lesion by applying an AI diagnosis model to the obtained one or more MR images of the organ of the patient;

determining, based on the diagnosis, a treatment plan for said lesion, said treatment plan including a series of instructions for a user to attach one or more treatment tools to said surgical robot device and control instructions for navigating said surgical robotic device through an in-bore pathway to be positioned to perform an in-bore treatment on the lesion; and performing, by the surgical robotic device, said in-bore treatment on the lesion based on the treatment plan.

* * * * *